United States Patent [19]
Nallakrishnan

[11] Patent Number: 5,752,960
[45] Date of Patent: May 19, 1998

[54] INTRAOCULAR LENS INSERTION FORCEPS

[76] Inventor: Ravi Nallakrishnan, 26 Plaza Dr., Westmont, Ill. 60559

[21] Appl. No.: 655,955

[22] Filed: May 31, 1996

[51] Int. Cl.⁶ .................................................. A61F 9/00
[52] U.S. Cl. ................................... 606/107; 606/205
[58] Field of Search .............................. 606/107, 127, 606/205–211; 623/4, 6

[56] References Cited

U.S. PATENT DOCUMENTS

| | | | |
|---|---|---|---|
| 4,813,957 | 3/1989 | McDonald | 623/6 |
| 4,959,070 | 9/1990 | McDonald | 623/6 |
| 5,007,913 | 4/1991 | Dulebohn et al. | 606/107 |
| 5,135,530 | 8/1992 | Lehmer | 606/107 |
| 5,178,622 | 1/1993 | Lehner | 606/107 |
| 5,292,324 | 3/1994 | McDonald | 606/107 |
| 5,591,176 | 1/1997 | Henderson et al. | 606/208 |

*Primary Examiner*—Glenn K. Dawson
*Attorney, Agent, or Firm*—Jerry A. Schulman

[57] ABSTRACT

A forceps for implanting an intraocular lens into an eye through a slit in the eye wall has opposed, direct-action jaws, spring-biased to a position opening the jaws, that allows the jaws to open to a distance large enough to release the lens while providing an intermediate arm structure that opens to a distance about half that of the jaws, allowing the lens to be inserted and released through a relatively small incision.

14 Claims, 2 Drawing Sheets

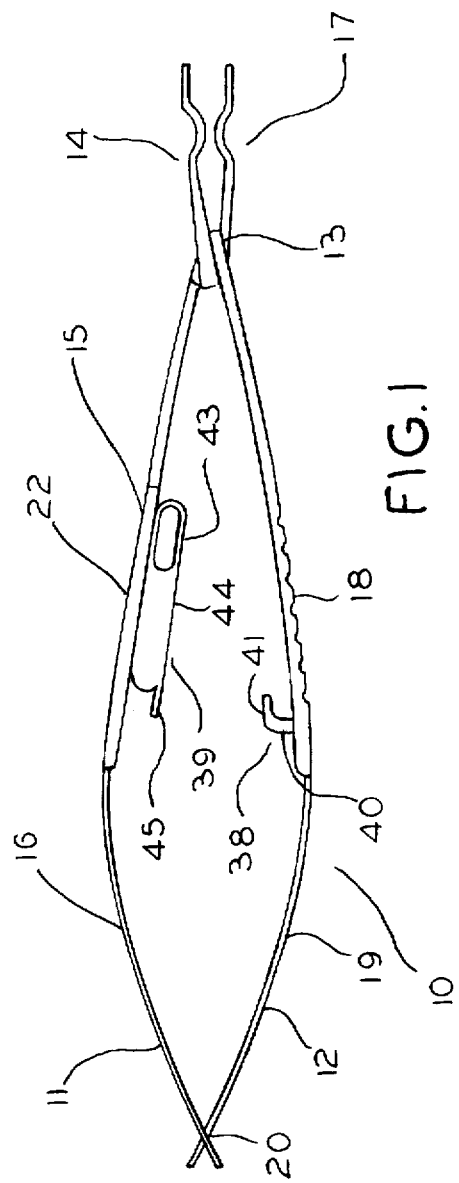
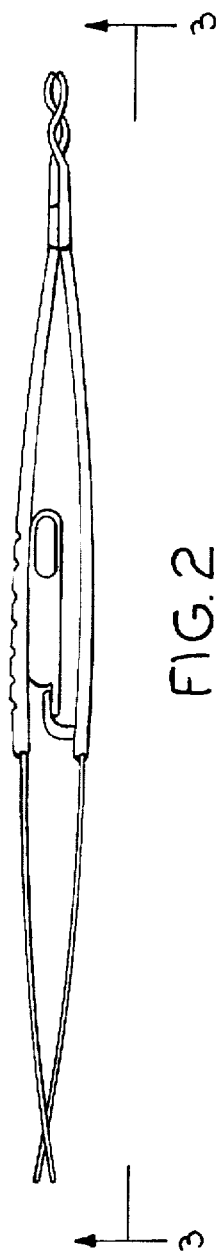
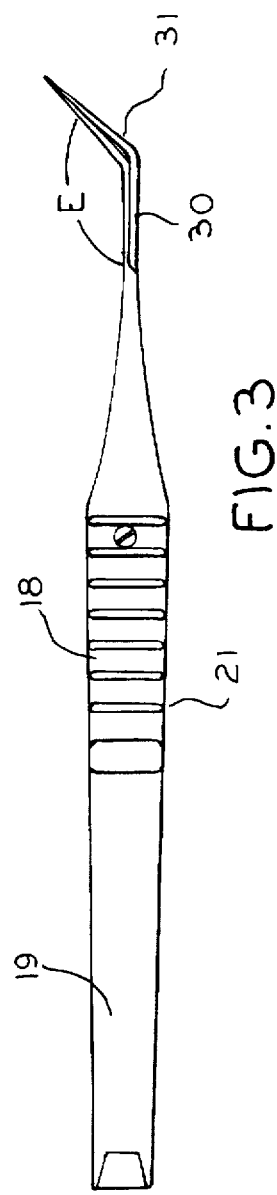
FIG.1
FIG.2
FIG.3

INTRAOCULAR LENS INSERTION FORCEPS

BACKGROUND OF THE INVENTION

This invention relates generally to instruments used in ophthalmological surgery and, more particularly, to forceps used to grip or hold a folded intraocular replacement lens and insert it through an incision made in the eye.

It is a well-known ophthalmic procedure to replace a damaged or diseased eye lens with an intraocular lens (IOL) made from synthetic materials such as silicone compounds. In its most common form, an IOL generally replicates the somewhat disk-like shape of the eye's normal lens. A pair of curved, extruded plastic strands called haptics are attached to the IOL to aid in centering it in the eye and to keep the IOL from turning after it has been implanted. A description of such a lens and the procedure to install it is set forth in U.S. Pat. No. 4,844,093 (Jampel, et al.) and is partially incorporated below.

As originally practiced, human eye lens replacement involved the use of artificial IOLs made from hard plastic and formed in a generally disk-like shape to match the contours of a human lens. A preferred surgical technique for removal of a defective natural lens and insertion of a replacement, artificial IOL usually involves removing the natural lens through an incision or slit cut in the limbus or margin of the cornea of the eye. As an example, one technique for removing the natural lens is to emulsify it with an ultrasonic probe and remove the lens segments by suction through the incision. The same incision is then used to insert the IOL into the posterior chamber of the eye where it must be positioned in the place of the natural lens. The incision is then closed and allowed to heal.

In the past, synthetic IOLs were made of a rigid material and were sized and shaped to fit within the posterior chamber of the eye in place of the natural lens. To insert the rigid lens the surgeon was required to make a relatively substantial incision, on the order of about 6 to 7 millimeters. With the development of resilient flexible or foldable synthetic plastic IOLs, eye surgeons have developed surgical techniques which call for a much smaller incision through which the flexible IOLs may be inserted after having been rolled or folded. As an example, an incision of roughly 3–4 millimeters may be large enough to insert a rolled or folded lens. After the folded lens is inserted through the smaller incision into the posterior chamber for subsequent positioning into the sulcus or capsule, the IOL is allowed to resiliently return to its normal, disklike unfolded shape.

Smaller incisions heal faster, reduce the risk of astigmatism, require no sutures and induce less postoperative inflammation, all of which are of substantial benefit to the patient and all of which result from use of foldable lenses instead of rigid lenses.

However, as with most advances in medicine, new techniques introduce new problems to solve. Foldable IOLs are delicate and can be damaged when being handled and folded. There is the risk of damage to the eye tissues during the insertion operation. Where the marginal edges of the foldable IOLs are more delicate or thinner than the main body portion of the lenses, the edges may be easily damaged. Successful implementation of soft, foldable IOLs requires techniques and instruments making it possible to fold a lens, hold it in folded condition, insert it through the eye incision into the posterior chamber and allow it to unfold and center itself without significant damage or scratching to either the lens or the eye tissues.

Another desirable aspect of this implantation technique is to be able to insert the folded lens through as small an incision as possible, requiring an insertion forceps which not only allows insertion of a folded IOL, but also allows the lens to be unfolded, once inserted, with an action that can be carried out without compromising the relatively small incision or requiring the incision to be enlarged.

One way of carrying out such an action is through use of a "cross-action" forceps construction. Within the context of the present invention, the term "cross-action" refers to a type of forceps constructed such that the action of the handle produces an opposite action at the jaws. e.g., closing the handles of the forceps opens the forceps jaws. A series of patents issued to Henry H. McDonald illustrates this type of construction.

U.S. Pat. No. 4,813,957 (McDonald) teaches and describes a method for IOL implantation using a cross-over forceps with the cross-over positioned at the incision.

U.S. Pat. No. 4,959,070 (McDonald) teaches and describes a cross-action insertion forceps with arms that cross over as the jaws are moved from the closed to the open position.

U.S. Pat. No. 5,292,324 (McDonald) teaches and describes an endwise adjustable forceps for lens implantation in eye having a cross-over point that shifts position as the jaws are opened and closed.

As the McDonald references demonstrate, the cross-action forceps described are biased to remain normally in the closed position, that is, biased to force the handles apart to keep the jaws in the closed position. This adds an additional amount of force that must be overcome to squeeze the forceps handles to open the jaws, release the lens and allow it to unfold. Squeezing on the handles with sufficient force to open them may allow the lens to pop open or "explode" into position. It has also been noted that present cross-action forceps still have the capacity to stretch the incision when the rear portion of the jaws, positioned within the incision, separate as the front or distal ends of the jaws are allowed to separate to a distance sufficient to allow the folded lens to unfold into position. It is desirable to allow the forceps jaw ends to open as widely as possible with as small a concurrent separation as possible between those portions of the jaws positioned within the incision. The present invention allows the jaws to separate to a distance approximately twice that of the legs that are positioned within the incision to release the lens in a non-explosive fashion without compromising the small incision wound, while retaining the desirable aspects of using a direct-action tool.

Past direct-action forceps generally include straight jaw legs that extend from the pivot point of the forceps to the end of the jaws. As the jaw ends are separated, the jaw legs also separate relatively widely, requiring a larger incision or stretching or compromising the incision.

The present invention relates to a hand-held forceps usable to hold an IOL for insertion into and release within the eye which uses a direct action arrangement, i.e., an action which closes the jaws when the handles are closed and wherein the jaws are normally biased to remain in the open position and where force is applied to the forceps handles to close the forceps and grip the folded lens. To release and unfold the lens, the handles are gradually allowed to part against the combined force of the lens unfolding and the handle spring urging the handles to the open position. This allows a more controlled release to avoid the tendency of the lens to "explode" into position.

A pair of opposed, upper and lower arms terminate in blade portions within which the IOL is held. Each arm is formed with a first, generally straight portion, a second portion curving generally downward (for the upper arm) and upward (for the lower arm), a third portion curving generally upward (for the upper arm) and downward (for the lower arm) and a fourth portion which forms an upper lens-holding blade (for the upper arm) and a lower lens-holding blade (for the lower arm). The first and second arm portions are joined at a pivot and extend beyond the pivot to form a pair of opposed handles terminating in spring steel straps joined one to another at their ends and biased to keep the upper and lower blades normally apart, or in the "open" position. As the handles are squeezed toward each other, the upper and lower blades also move toward one another, remaining generally parallel to each other as they do so. As the blades are moved progressively closer to one another, the second and third portions of each arm progressively overlap in a manner that keeps the maximum separation distance of the arms small enough to remain within the incision without widening it. The curved arm portions and the blades are constructed in a manner that allows the blades to reach a maximum open dimension larger than the maximum distance apart of the second and third upper and lower arm portions, with the blade open dimension being about twice that of the distance apart of the second and third upper and lower arm portions. The blades on the end of the arms are "bullet-shaped" to allow the blades, when closed, to smoothly enter the incision. A lock may be provided on the handle portions to keep the forceps in the locked position to hold a folded lens firmly. Release of the lens is thus carried out by releasing the handles, resulting in a more easily controlled rate of release, while avoiding the undesirable tendency of direct-action tools to require a relatively large displacement at the back of the jaws to allow the front of the jaws to separate fully enough to release the lens into the eye in a non-explosive fashion.

BRIEF DESCRIPTION OF THE DRAWINGS

These and further aspects of the present invention will become more apparent upon considering the accompanying drawings, in which:

FIG. 1 is a lateral view of a forceps embodying the present invention, with the jaws in the full open position;

FIG. 2 is a lateral view of the embodiment of FIG. 1 with the jaws in the full closed position;

FIG. 3 is a view taken along 2—2 of FIG. 2, illustrating the angle between the jaws and the handle;

DETAILED DESCRIPTION OF THE DRAWINGS

Figure 4:
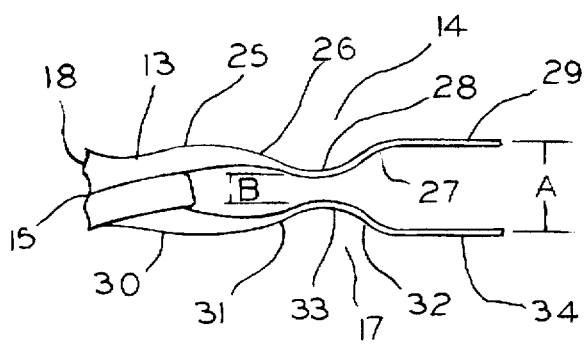
FIG. 4 is an enlarged detail of the jaws of FIG. 1.

Referring now to FIG. 1, the numeral 10 indicates generally an IOL insertion forceps consisting generally of a upper arm 11 and a lower arm 12 joined together at a pivot 13. Upper arm 11 consists of a jaw portion 14, a handle portion 15 and a spring portion 16, while lower arm 12 consists of a jaw portion 17, a handle portion 18 and a spring portion 19. Upper and lower spring portions 16 and 19 are joined at a spring lock 20 to bias handle portions 15 and 18 and, thereby, jaw portions 14 and 17 apart from each other when unstressed.

As seen in FIG. 3, lower handle 18 is generally rectangular and has a series of handle grips 21 molded into lower handle 18. A similar set of grips 22 are also formed on upper handle 15, as indicated in FIG. 1. Also shown in FIG. 3 is a detail of spring lock 20, showing a window 23 formed in lower spring 19 and a tab 24 formed at the end of upper spring 16 sized and shaped to fit through and engage window 22.

Referring to FIG. 4, there is shown an enlarged detail of upper and lower jaws 14 and 17, joined at pivot 13, in the full open position. Upper jaw 14 has a first leg 25 integral with and extending from upper handle 15, a second leg 26 integral with first leg 25 and extending toward lower jaw 17, a third leg 27 integrally joined with second leg 26 at bight 28 and extending away from lower jaw 17, and terminating in upper blade 29. In like fashion, lower jaw 17 has a first leg 30 integral with and extending from lower handle 18, a second leg 31 integral with first leg 30 and extending toward upper jaw 14, a third leg 32 integrally joined with second leg 31 at bight 33 and extending away from upper jaw 14, and terminating in lower blade 34.

When in the full open position, jaws 14 and 17 do not overlap at all, and blades 29 and 34 are spaced apart by distance A. At the same time, bights 28 and 33 are spaced apart by distance B, a distance significantly less than distance A. Preferably, distance A is about 6–7 mm., while distance B is about 3 mm. As can also be seen, the distance apart between legs 26 and 31, and legs 27 and 32 gradually increases from B at bights 28 and 33 to a dimension approaching A.

Figure 5:
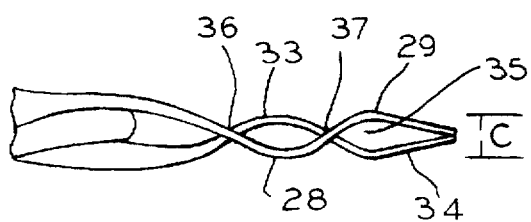
FIG. 5 is an enlarged detail of the jaws of FIG. 2.

Referring now to FIGS. 2 and 5, jaws 14 and 17 are shown in the full closed position, the position forceps 10 would be in when gripping an IOL for insertion. Blades 29 and 34 meet at their tips and thus define between them an IOL receiving slot or channel 35 within which the folded IOL is held. In the closed position, jaws 14 and 17 overlap at first and second overlap points 36 and 37. Lower bight 33 is now located beneath upper bight 28, and jaws 14 and 17 are compressed to an approximate distance apart C from blades 29 and 34 to a point slightly past overlap point 36 when moving in a direction toward the handle end of forceps 10. Distance C is preferably about 3 mm., a size allowing the insertion of the IOL through an incision of approximately 3–4 mm.

As seen in FIG. 1, when springs 16 and 19 are unstressed, handles 18 and 22 are held their farthest distance apart and jaws 14 and 17 are in their full open position. To move jaws 14 and 17 to the closed position, handles 15 and 18 are gripped and manually compressed toward one another, an action which straightens springs 16 and 19. This straightening stresses springs 16 and 19 which then oppose the closing action, creating a biasing force tending to force handles 18 and 22 apart when they are released.

Figure 6:
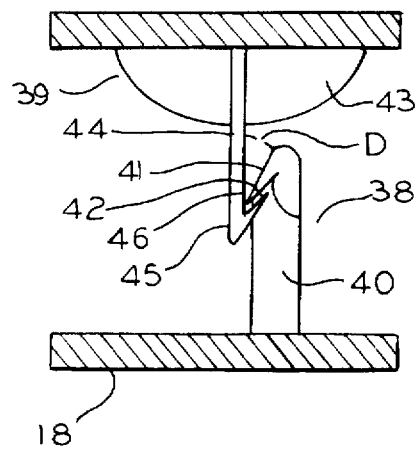
FIG. 6 is a view along 6—6 of FIG. 2.

In order to overcome this biasing force and hold jaws 14 and 17 in a closed position to hold an IOL for insertion, another preferred embodiment provides a handle lock, consisting of a locking hook 38 and a locking bracket 39. As seen in FIGS. 1 and 6, hook 38 has a depending peg 40 integrally attached to handle 18 and a blade 41 integrally formed with and extending generally perpendicular from peg 39 at an angle D thereto and terminating in a lower blade edge 42. Bracket 39 has a mount 43 integrally attached to handle 15 from which a tongue 44 extends rearwardly in the direction of spring 16. Tongue 44 terminates in a proboscis 45 having an inverted V-shaped channel 46 formed by folding over a portion of proboscis 45.

Handles 15 and 18 are locked in a closed position by moving them toward one another until blade 41 is moved past proboscis 45. Handles 15 and 18 are then allowed to move slightly toward the open position while aligning blade edge 42 to engage channel 46. To release handles 15 and 18 from the locked position, the handles are slightly compressed to move blade edge 42 out of channel 46 and then moved slightly laterally to allow blade edge 42 to clear channel 46 as handles 15 and 18 are urged apart by the action of springs 16 and 19.

Referring again to FIG. 3, it can be seen that jaws 14 and 17 are inclined at an angle E with respect to handles 15 and 18 and, more specifically, that first legs 30 and 25 (not shown in FIG. 3) is inclined with respect to second legs 31 and 26 (not shown in FIG. 3). Angle E is about 45° to facilitate positioning of forceps 10 for insertion of an IOL.

Figure 7:
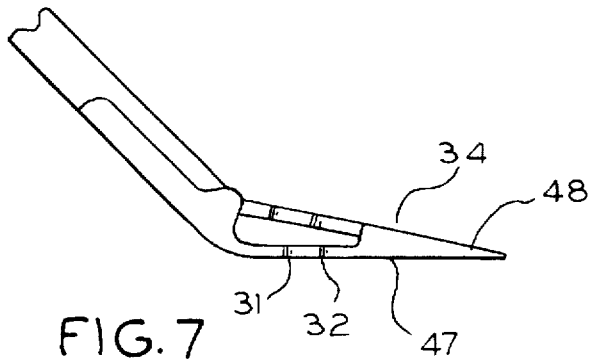
FIG. 7 is an enlarged view of the circled portion of FIG. 3, showing the contours of the jaws in the closed position.
Figure 8:
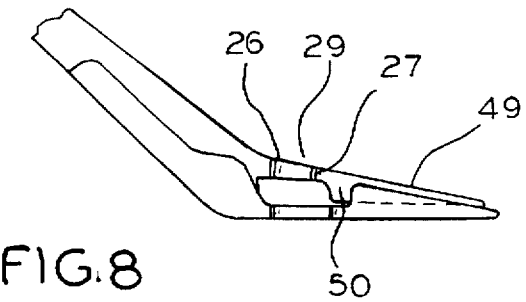
FIG. 8 is a view of the jaws in FIG. 7 shown in the opened position.

Referring now to FIGS. 7 and 8, another aspect of the jaw blade construction is shown. FIG. 7 shows an enlarged view of the lateral aspect of lower blade 34, showing the blade to have a straight portion 47 generally coextensive with second and third legs 31 and 32, and a generally triangular portion 48 integral with and extending upward from straight portion 48. FIG. 8 shows that upper blade 29 is formed with a corresponding shape, having a straight portion 49 generally coextensive with second and third legs 26 and 27 and a generally triangular portion 50 integral with and extending downward from straight portion 49. As FIG. 8 illustrates, triangular portions 48 and 50 extend in opposite directions, i.e., triangular portion 48 extends upward to overlap the straight portion 49 of upper blade 29, while triangular portion 50 extends generally downward to overlap the straight portion 47 of lower blade 34. This creates a smooth, "bullet-shaped" profile when the blades are closed, allowing the blades to easily pass through the incision.

A preferred use of the present invention begins with jaws 14 and 17 in the full open position as shown in FIG. 1. An IOL to be inserted is placed in a folding block or folding forceps and is folded over into position for insertion. Forceps 10 is then used to grip the folded IOL by positioning blades 29 and 34 on either side of the folded IOL and thereafter manipulating handles 15 and 18 to close jaws 29 and 34, positioning the folded IOL in receiving channel 35. Handles 15 and 18 are next manipulated further to engage blade edge 42 in channel 46, thereby locking forceps 10.

Next, forceps 10 is maneuvered to extend jaws 14 and 17 through an incision already formed in the limbus or margin of the cornea of the eye. Preferably, forceps 10 is inserted far enough to position bights 28 and 33 proximate the slit. To install the IOL, the surgeon next manipulates handles 15 and 18 to release blade edge 42 from channel 46 and slowly releasing handles 15 and 18 against the biasing force of springs 16 and 19 to allow the IOL to unfold in a controlled manner. As seen in FIG. 4, blades 29 and 34 can open to a distance significantly larger than the size of the insertion, in approximately a 2:1 ratio, facilitating release of the IOL.

It is believed that allowing release of the IOL to occur by releasing rather than compressing handles 15 and 18 (as required by the use of cross-action forceps) results in a more controlled and efficient unfolding of the IOL and avoids the tendency of the lens to explode into position when released too abruptly.

After positioning and release of the IOL is completed, jaws 29 and 34 are closed to allow them to be withdrawn through the incision, and insertion is then complete.

It should be noted that bights 28 and 33 need not be positioned exactly at the incision: there is a certain amount of leeway created by the curving and dimensioning of legs 26, 27, 31 and 32 such that the distance apart of these elements will still be less than the size of the incision, even though greater than dimension B of FIG. 4.

While the foregoing has presented a description of a preferred embodiment of the present invention, it is to be understood that this description is presented by way of example only and is not intended to limit the scope of the present invention. It is expected that others skilled in the art will perceive variations which, while differing from the foregoing, do not depart from the spirit and scope of the invention as herein described and claimed.

I claim:

1. An instrument for the insertion of an intraocular lens, said instrument comprising:

first and second handles, said first handle having first and second ends and said second handle having first and second ends;

means for joining said first and second handles pivotally together proximate said first handle ends;

first and second means for gripping said intraocular lens, said first grip means extending from and integral with said first handle at said first handle first end;

said second grip means extending from and integral with said second handle at said second handle first end;

said first and second grip means movable away one from another to an open position and moveable one toward another to a closed position responsive to the pivoting of said first handle relative to said second handle;

said first grip means including a first leg integral with said first handle first end and curved toward said second grip means, a second leg integral with said first leg and curved away from said second grip means, said first and second legs meeting at and defining a first bight, said second leg terminating in a first lens holding jaw;

said second grip means including a third leg integral with said second handle first end and curved toward said first grip means, a fourth leg integral with said third leg and curved away from said first grip means, said third and fourth legs meeting at and defining a second bight, said third leg terminating in a second lens holding jaw, said first and second jaws in a substantially parallel and opposed spatial relationship, and said first and second grip means in a non-overlapping and opposed spatial relationship when said first and second grip means are in said open position; and means to bias said first and second handles to hold said first and second grip means in said open position.

2. The apparatus as recited in claim 1 wherein when said first and second grip means are in said open position, said jaws are positioned a distance A apart and said first and second legs and said third and fourth legs are, at their furthest separation one from another, positioned a distance B apart, said distance B being substantially less than said distance A.

3. The apparatus as recited in claim 2 wherein distance A is about 7 mm.

4. The apparatus as recited in claim 2 wherein said distance B is about 3 mm.

5. The apparatus as recited in claim 1 wherein when said first and second grip means are in said closed position, said first and second legs and said third and fourth legs are, at their furthest separation one from another, positioned a distance C apart, said distance C being approximately the same as the distance from said first jaw to said second jaw.

6. The apparatus as recited in claim 1 wherein, as said first and second grip means are moved one toward another to said closed position, said first and second legs progressively overlap said third and fourth legs.

7. The apparatus as recited in claim 1 wherein said instrument further includes means to lock said instrument in said closed position.

8. The apparatus as recited in claim 7 wherein said lock means includes a locking tongue attached to and spaced from and extending generally parallel to one said handle, said tongue having a V-shaped channel formed along one edge thereof; and a locking hook attached to the other of said handles, said locking hook having a locking arm integrally formed therewith spaced from and extending generally parallel to said other of said handles, said locking arm having a knife edge formed thereon.

said locking hook and said locking tongue being positioned to allow said knife edge to engage said channel when said handles are moved one toward another and, thereby, to hold said handles together.

9. The apparatus as recited in claim 1 wherein when said first and second grip means are in said closed position, said first and second jaws define therebetween a slot to receive said lens.

10. The apparatus as recited in claim 1 wherein said first jaw has an inner surface and an outer surface and a tip, said second jaw has an inner surface, and an outer surface and a tip, said inner surfaces spaced apart from and generally parallel one to another, said first jaw outer surface being generally triangular in shape with a first side of said triangle being generally coextensive with said second leg, a second side of said triangle being generally perpendicular to said second leg and extending in a first direction away from said second leg and a third side of said triangle extending from said second side to the tip of said first jaw;

said second jaw outer surface being generally triangular in shape with a first side of said triangle being generally coextensive with said fourth leg, a second side of said triangle being generally perpendicular to said fourth leg and extending in a direction away from said second leg opposite from said first direction and a third side of said triangle extending from said second side to the tip of said second jaw;

said outer surfaces being rounded, contoured and tapered from a minimum taper at said jaw tips to a maximum taper toward said second and fourth legs, respectively.

11. The apparatus as recited in claim 1 wherein said first and second grip means meet said first and second handles at an angle of about 45°.

12. The apparatus as recited in claim 1 wherein said biasing means is integrally formed with said first and second handles.

13. The apparatus as recited in claim 12 said biasing means includes a first spring strap having first and second ends, said first end of said first strap integrally attached to said second end of said first handle, a second spring strap having first and second ends, said first end of said second strap integrally attached to said second end of said second handle, said second end of said first strap attached to said second strap proximate the second end of said second strap.

14. The method of implanting a foldable intraocular lens in an eye, said method comprising the steps of:

(a) making a slit in the eye wall;

(b) providing a forceps having first and second handles, said first handle having first and second handle ends and said second handle having first and second handle ends;

means for joining said first and second handles pivotally together proximate said first handle ends;

first and second means for gripping said intraocular lens, said first grip means extending from and integral with said first handle at said first handle first end;

said second grip means extending from and integral with said second handle at said second handle first end;

said first and second grip means movable away from one another to an open position and moveable toward each other to a closed position responsive to the pivoting of said first handle relative to said second handle;

said first grip means terminating in a first lens holding jaw;

said second grip means terminating in a second lens holding jaw;

said first and second jaws in a substantially parallel and opposed spatial relationship, and said first and second grip means in a non-overlapping and opposed spatial relationship when said first and second grip means are in said open position; and means to bias said first and second handles to hold said first and second grip means in said open position;

(c) folding said lens;

(d) positioning said jaws about said lens;

(e) moving said handles one toward the other to grip said folded lens with said jaws;

(f) inserting said jaws and said lens through said slit;

(g) positioning said grip means at said slit; and (h) allowing said handles to move apart gradually to release said lens and allow said lens to unfold.

* * * * *